United States Patent [19]

Yajima et al.

[11] Patent Number: 4,950,418
[45] Date of Patent: Aug. 21, 1990

[54] REAGENT FOR REMOVING PROTECTIVE GROUPS IN PEPTIDE SYNTHESIS

[75] Inventors: Haruaki Yajima, Toyonaka; Nobutaka Fujii, Hirakata; Gilberto M. A. Guterres, Tokyo; Tatsuhiko Honguu, Yokohama, all of Japan

[73] Assignee: Shin Etsu, Chemical Co., Ltd., Japan

[21] Appl. No.: 386,005

[22] Filed: Jul. 25, 1989

Related U.S. Application Data

[63] Continuation of Ser. No. 104,070, Oct. 5, 1987, abandoned.

[30] Foreign Application Priority Data

Oct. 9, 1986 [JP] Japan ................... 61-239059

[51] Int. Cl.$^5$ .............................................. C09K 3/00
[52] U.S. Cl. ................................. 252/182.12; 530/335
[58] Field of Search .................... 252/182.12; 530/335

[56] References Cited

U.S. PATENT DOCUMENTS

| | | | |
|---|---|---|---|
| 4,368,150 | 1/1983 | Fujino et al. | 562/430 |
| 4,460,576 | 7/1984 | Kawauchi | 514/13 |
| 4,684,722 | 8/1987 | Sundeen | 540/203 |
| 4,689,404 | 8/1987 | Kawada et al. | 536/23 |
| 4,689,432 | 8/1987 | Tsien et al. | 562/435 |
| 4,696,945 | 9/1987 | Frei et al. | 514/450 |
| 4,707,541 | 11/1987 | Diaz et al. | 530/324 |
| 4,731,362 | 3/1988 | Hamashima et al. | 514/202 |
| 4,734,512 | 3/1988 | Kaneko et al. | 549/214 |

OTHER PUBLICATIONS

Fujii et al., *J. Chem. Soc., Chemical Communications*, 1987, (#4), 274–275, (Feb. 1987).

Fujii et al., *Chem. & Pharm. Bull.*, 35, (#3), 1266–1269, (Mar. 1987).

"Synthetic Studies on Peptides Using Organosulfonic Acids–Deprotecting Procedure", 103, Yakugaku Zasshi, 805–818, (1983).

"Acidolytic Deprotecting Procedures in Peptide Synthesis", H. Yajima and N. Fuji, The Peptides, vol. 5, 1983.

*Primary Examiner*—Edward A. Miller
*Attorney, Agent, or Firm*—Arnold, White & Durkee

[57] ABSTRACT

Reagent for removing protective groups employed in peptide synthesis comprises a combination of hard acid and soft base. The hard acid is trialkylsilyltrifluoromethanesulphonate $R_3SiO_3SCF_3$ and the soft base is ether. The reagent provides high efficiency of deprotection and has a low tendency to cause side reaction.

6 Claims, 3 Drawing Sheets

FIG. 2 Neuromedin U-25

```
                                          (CH3)3SiO3SCF3
                                         ↗
[6]  Z(OMe)-Phe-Lys(Z)-NHNH2
[5]  Z(OMe)-Val-Asp(OBzl)-Glu(OBzl)-Phe-NHNH-Troc
[4]  Z(OMe)-Gln-Gly-NHNH2
[3]  Z(OMe)-Pro-Ile-Val-Ser-NHNH2
[2]  Z(OMe)-Gln-Asn-Arg(Mts)-Arg(Mts)-NHNH2
[1]  H-Tyr-Phe-Leu-Phe-Arg(Mts)-Pro-Arg(Mts)-Asn-NH2

H-Phe-Lys-Val-Asp-Glu-Glu-Phe-Gln-Gly-Pro-Ile-Val-Ser-Gln-Asn-Arg-Arg-
Tyr-Phe-Leu-Phe-Arg-Pro-Arg-Asn-NH2
```

FIG. 3 Rabbit Stomach Peptide

```
            OBzl
             |
(a)  Z(OMe)-Pyr-Val-Asp-Pro-Asn-Ile-Gln-Ala-④
             (CH3)3SiO3SCF3
              ─────────────→
(b)         H-Pyr-Val-Asp-Pro-Asn-Ile-Gln-Ala-OH
```

FIG. 4
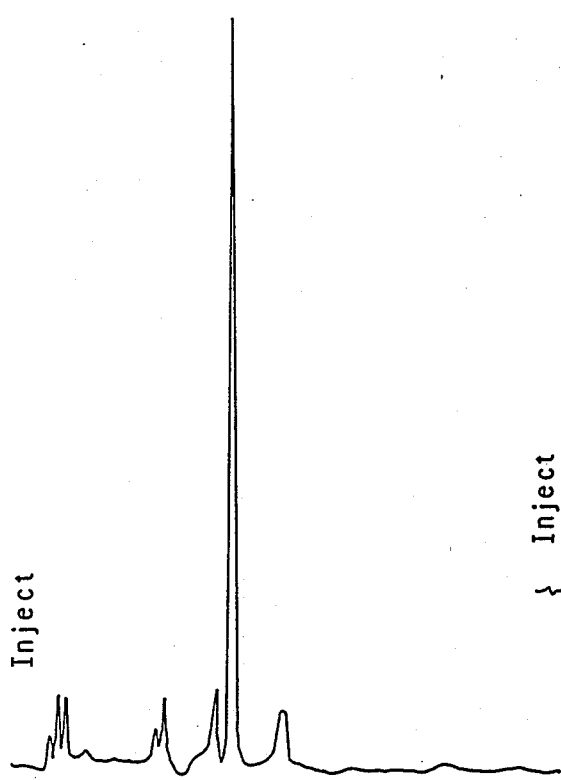
FIG. 6
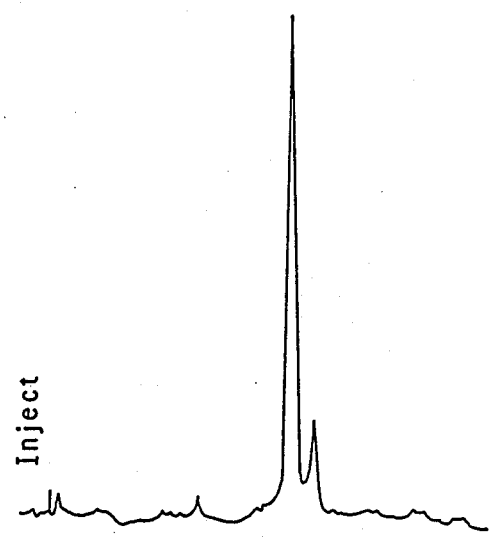
FIG. 5 Galanin
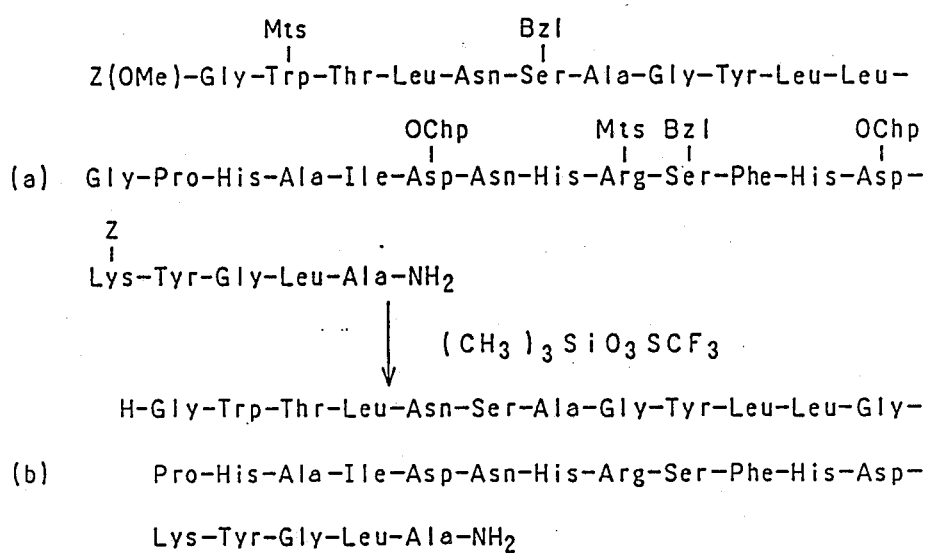

REAGENT FOR REMOVING PROTECTIVE GROUPS IN PEPTIDE SYNTHESIS

This is a Continuation of application Ser. No. 07/104,070 filed Oct. 5, 1987, now abandoned.

BACKGROUND OF THE INVENTION

The present invention relates to reagent for removing protective groups attached to amino acids during peptide synthesis.

In peptide synthesis, it is important to remove or cleave protective groups attached to amino acid at the final stage thereof and this removing reaction exerts a great influence on the result of such peptide synthesis. Hitherto, hydrogen fluoride has generally been used as reagent for removing protective groups, i.e., departing reagent.

However, it is required to strictly select containers and implements for handling hydrogen fluoride since it has high corrosive properties. For instance, a container or the like made of glass cannot be used and it has been obliged to employ those of fluoroplastics. Besides, hydrogen fluoride is harmful to human and, therefore, cautions for handling the same are necessary. Moreover, the use of hydrogen fluoride as the reagent for removing protective groups leads to the increase in by-products due to side reactions.

Under such circumstances, we, the inventors of this invention have conducted various studies to develop reagent for removing protective groups in place of hydrogen fluoride currently employed. As a result of the studies, we found out reagent comprising a combination of hard acid and soft base on the basis of the principle of hard-soft acid-base, the detail of which is disclosed in YAKUGAKU ZASSHI (J. Pharm. Soc. Japan), 1983, 103, 805-818. The method disclosed in this article comprises employing the combination of trifluoromethanesulfonic acid ($CF_3SO_3H$) as the hard acid with thioanisole as the soft base and carrying out the removal of protective groups under acidic condition. As trifluoromethanesulfonic acid used in this reaction is less harmful to humans compared with hydrogen fluoride, we may use cheap equipment. As side reaction is low possibility, we can get peptide by high yield. However, trifluoromethanesulfonic acid is fumy and very difficult to handle. Therefore, the reagent improved has been wanted.

SUMMARY OF THE INVENTION

We, the inventors of this invention, have continued the studies to develop reagent for removing protective groups and we found that trialkylsilyltrifluoromethanesulfonate $R_3SiO_3SCF_3$, i.e., trialkylsilyl triflate may be used instead of trifluoromethanesulfonic acid as the hard acid. Trialkylsilyl triflate has widely been employed in organic synthesis as a strong silylating agent.

The reagent for removing protective groups employed in peptide synthesis of the present invention, which is completed on the basis of the above-mentioned findings, comprises a combination of hard acid and soft base and is characterized in that the hard acid is trialkylsilyltrifluoromethanesulphonate represented by the general formula $R_3SiO_3SCF_3$ and that the soft base is ether. The R is an alkyl group.

Preferred examples of the alkyl group R inlcude a lower alkyl group such as methyl group, ethyl group and propyl group. The trialkylsilyltrifluoromethanesulphonate in which the substituent R is methyl, i.e., trimethylsilyltrifluoromethanesulfonate is particularly preferred since it has excellent properties and has been industrially mass-produced as asilylating agent. Examples of ethers as the soft base include anisole, thioanisole and diphenyl-sulfide and particularly preferred is thioanisole because it seldom causes side reactions.

Trialkylsilyltrifluoromethanesulphonate is an organic silicon compound which is chemically modified with trifluoromethanesulfonic acid as the strongest organic acid. For example, the silicon atom in trimethylsilyltrifluoromethanesulfonate presents $^{29}Si$ NMR chemical shift ($\delta$) of 46.1 ppm in a solvent (trifluoroacetic acid $CF_3COOH$). As seen from the value of $\delta$, the electron density thereof is extremely lowered due to the strong electron attractive effect of trifluoromethanesulfonyl group. The high electron deficiency surely results in the strong inter-action between the silicon atom in the hard acid (trialkylsilyltrifluoromethanesulfonate) and a hetero atom in a protective group interested.

It is another characteristic of the trialkylsilyltrifluoromethanesulphonate that the only groups $CF_3SO_3^-$, which is dissociated when the sulfonate attacks such a hetero atom, is an extremely weak base or a nucleophilic species. For this reason, the occurrence of side reactions is suppressed when the trialkylsilyltrifluoromethanesulphonate is used as reagent for removing protective groups and this makes it more effective than hydrogen fluoride as the deprotecting reagent. This fact was practically evidenced experimentally utilizing amino acid derivatives.

FIG. 1 shows a reaction mechanism in which a benzyl type protective group $$-CH_2-\phenyl$$

is removed from an amino acid derivative $$Ami-CH_2-O-CH_2-\phenyl$$

in a trifluoroacetic acid system containing the combination of trimethylsilyltrifluoromethanesulfonate $(CH_3)_3SiO_3SCF_3$ as the hard acid with thioanisole $$\phenyl-S-CH_3$$

as the soft base.

As explained above, the reagent for removing protective groups according to the present invention provides high efficiency of deprotection and has a low tendency of causing side reaction. Therefore, the reagent of the present invention is very useful means for synthesizing peptides, proteins and enzymes.

Moreover, the reagent of the invention has no corrosive properties and is easy to handle, thus it never requires the use of containers and implements of a specific material. In addition, it is relatively safe to human health. Besides, it is the reagent of general-purpose properties or widely used and thus is easily available. Therefore, it is useful for reducing cost for investment and mass production of peptides while saving cost.

BRIEF DESCRIPTION OF THE DRAWINGS

FIG. 2 is a diagram which illustrates the synthesis of Neuromedin U-25.

FIG. 3 is a diagram for illustrating the synthesis of the Rabbit Stomach Peptide.

FIG. 4 is a chart of high performance liquid chromatography of the Rabbit Stomach Peptide.

FIG. 5 is a diagram illustrating the synthesis of Galanin.

FIG. 6 is a chromatogram of Galanin according to high performance liquid chromatography.

FIG. 7 is a diagram showing the synthesis of Urotensin II.

FIG. 8 is a chromatogram of Urotensin II obtained by high performance liquid chromatography.

DESCRIPTION OF THE PREFERRED EMBODIMENTS

Figure 1:
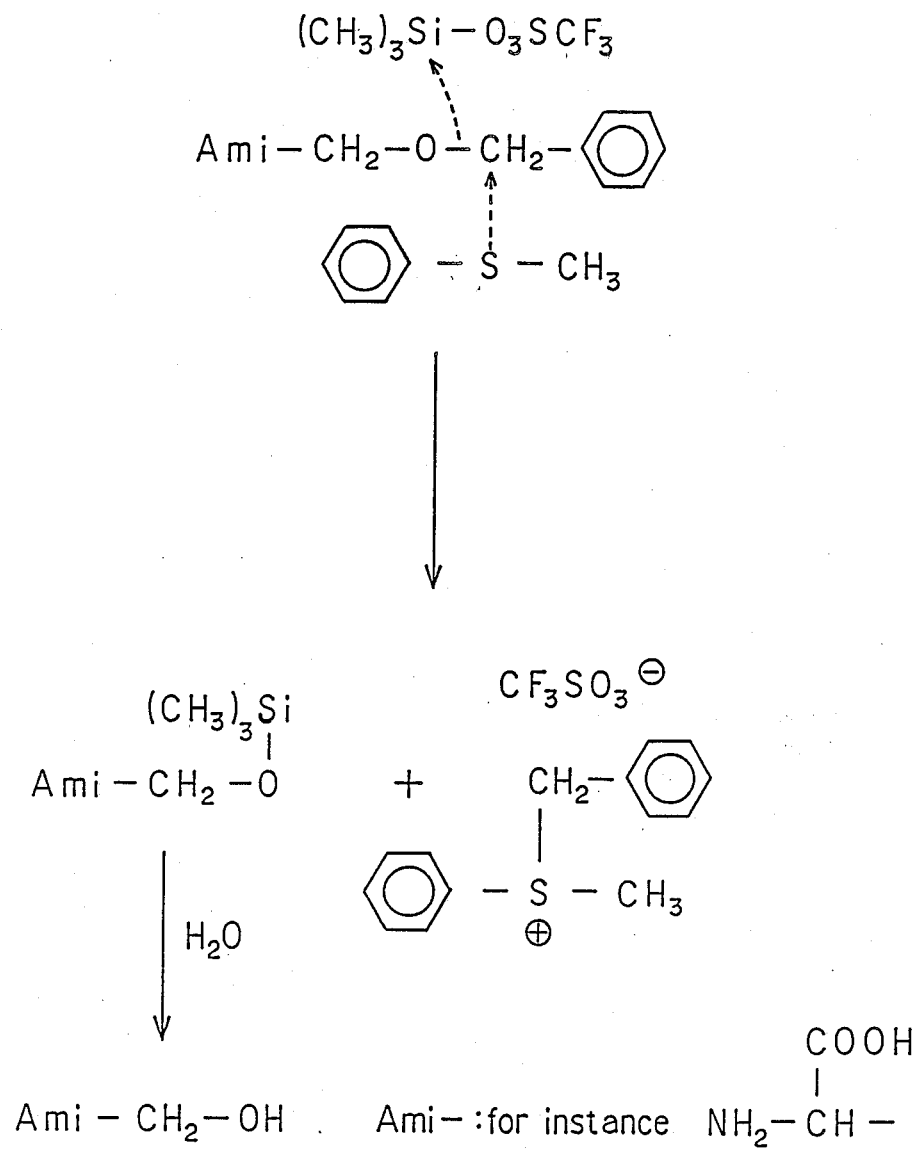
FIG. 1 is a diagram for illustrating the reaction for removing protective groups from an amino acid derivative.

In order to remove protective groups attached to the amino acid using the above-said trialkylsilyltrifluoromethanesulphonate as the hard acid and the ether as the soft base, it is sufficient to treat an objective material in a solvent (for instance, trifluoroacetic acid) while both these reagents coexist therein.

In this regard, the trialkylsilyltrifluoromethanesulphonate as the hard acid may be used in the form of solid phase comprising a solid support material X to which hard acid is fixed such as $R_3SiO_3SCF_2$—X.

As already explained above, the occurrence of side reaction is suppressed when the reagent according to the present invention is used. However, it is more effective to add a primary alcohol or a polyol such as meta-cresol, ethanediol and dithiothreitol in order to suppress the formation of by-products due to side reactions. These alcohols serve to capture alkyl cations formed during the deprotecting reaction. The capture of such alkyl cations results in the formation of desired peptides in high yield and high purity because of he inhibition of intramolecular rearrangement and the like.

DEPROTECTION OF AMINO ACIDS

For the purpose of examining the reagents of the present invention on the function of removing protective groups, various kinds of amino acids having a variety of protective groups were treated with 1M trimethylsilyltrifluoromethanesulfonate and thioanisole (1:1) in trifluoroacetic acid with the presence of 10 eq. meta-cresol at ice-bath temperature. Results obtained by periodically analyzing the amount of free amino acid during the deprotecting reaction are shown in Table 1.

TABLE 1

| Amino Acid Derivatives | Recovery of Amino Acid (%) | | |
|---|---|---|---|
| | 10 min. | 30 min. | 60 min. |
| Z(OMe)-Lys(Z)-OH | 93.6 | 98.7 | |
| Z(OMe)-Ser(Bzl)-OH | 90.6 | 91.7 | |
| Boc-Thr(Bzl)-OH | 98.0 | | |
| Z(OMe)-Glu(OBzl)-OH | 100.0 | | |
| Z(OMe)-Asp(OBzl)-OH | 99.2 | | |
| Boc-Asp(OChp)-OH | 85.6 | 88.9 | 90.4 |
| Boc-Tyr(Bzl)-OH | 85.6 | 88.9 | 90.4 |

TABLE 1-continued

| Amino Acid Derivatives | Recovery of Amino Acid (%) | | |
|---|---|---|---|
| | 10 min. | 30 min. | 60 min. |
| Boc-Tyr(Bzl)-OH * | 89.9 | | |
| Boc-Try(Cl$_2$-Bzl)-OH * | 87.3 | | |
| Boc-His(Tos)-OH | 94.5 | | |
| Boc-His(Bom)-OH | 88.9 | | |
| Boc-Trp(Mts)-OH ** | 100.0 | | |
| Z(OMe)-Arg(Mts)-OH | 97.6 | | |
| Z(OMe)-Arg(MBS)-OH | 75.5 | 93.5 | 94.2 |
| Z-Arg(Tos)-OH | 31.3 | 62.1 | 85.8 |
| Z-Arg(NO$_2$)-OH | 8.6 | 11.0 | 14.7 |
| H-Cys(MBzl)-OH | 95.4 | | |
| Boc-Cys(Bu$^t$)-OH | 79.5 | 87.3 | 96.8 |
| H-Cys(Ad)-OH | 100.0 | | |
| H-Cys(Bzl)-OH | 0 | | |
| Boc-Cys(Acm)-OH | 0 | | |
| Z(OMe)-Met(0)-OH | 17.8 | 27.6 | 44.2 |

In the table 1,
* This means that no other product is included.
** This deprotecting reaction is carried out in the presence of 10 eq. of ethanediol.

Each abbreviation appearing in the Table 1 is as follows:

Protective Groups

Z: benzyloxycarbonyl
Z(OHe): p-methoxybenzyloxycarbonyl
Boc: tert-butoxycarbonyl
Bzl: benzyl
Cl$_2$-Bzl: 2,6-dichlorobenzyl
Tos: p-toluenesulfonyl
Mts: mesitylenesulfonyl
MBS: p-methoxybenzenesulfonyl
Bom: benzyloxymethyl
MBzl: p-methoxybenzyl
Bu$^t$: tert-butyl
Ad: 1-adamantyl
Acm: acetamidomethyl
Troc: 2,2,2-trichloroethyloxycarbonyl Amino Acids Ala: alanine
Arg: arginine
Asn: asparagine
Asp: aspartic acid
Cys: cysteine
Gln: glutamine
Glu: glutamic acid
Gly: glycine
His: histidine
Ile: isoleucine
Leu: leucine
Lys: lysine
Met: methionine
Phe: phenylalanine
Pro: proline
Ser: serine
Thr: threonine
Tyr: tyrosine
TRp: tryptophane
Val: valine As seen from the results listed in Table 1, protective groups of α-amino acids such as Boc, Z(OMe), Z group attached to the side chain of Lys(Z) and also Bzl or OBzl attached to Ser, Thr, Glu or Asp were quantitatively removed within 10 minutes. The Chp group of Asp, which is an ester group of a secondary alcohol, was removed within 30 minutes at 0° C. and Tyr can be recovered approximately quantitatively from Tyr(Bzl)

or Tyr(Cl-Bzl) at 0° C. within 10 minutes without forming 3-Bzl-Try as a by-product. The removal of the group Mts from Trp(Mts) was carried out under the presence of 10 eq. ethanedithiol as the alkyl cation catcher and thus Trp was quantitatively recovered without causing alkylation of indole ring as a side reaction.

The recovery of His from His(Tos) or His(Bom) and that of Arg from Arg(Mts) or Arg(MBS) were quantitatively achieved by the treatment for 10 to 30 minutes at 0° C. On the other hand, the removal of the group $N^G$—$NO_2$ from Arg($NO_2$) resisted to the action of the reagents according to the present invention as in the case of trifluoromethanesulfonic acid $CF_3SO_3H$ and thioanisole/trifluoroacetic acid system, however, the $N^G$-Tos group in Arg(Tos) was removed by the treatment for 120 minutes. With respect to the removal of protective groups for sulfhydryl group of Cys, the groups MBzl, $Bu^t$ and Ad were quantitatively removed, however, the groups Bzl and Acm were not removed. In addition, Met(O) was reduced to Met in a rate of about 44.2% by the treatment for 60 minutes.

As a comparative example, Tyr(Bzl) was treated with a deprotecting reagent of 1M trimethylsilyltrifluoromethanesulfonate and thioanisle/trifluoroacetic acid from which anisole is removed to get Tyr. The yield of Tyr after 10 minutes was 64% and the formation of 3-Bzl-Tyr due to rearrangement was observed. The same reaction was repeated except that hydrogen fluoride was used in place of trimethylsilyltrifluoromethanesulfonate, then Tyr was recovered in an yield of approximately 100% within 10 minutes. However, the product contained 35% of 3-Bzl-Tyr as a by-product.

Examples in which protective groups attached to amino acids at the final stage of peptide synthesis are removed with the reagent according to the present invention will hereunder be explained.

DEPROTECTION IN SYNTHESIS OF NEUROMEDIN U-25

Neuromedin U-25 is a peptide comprised of 25 residues of amino acid which was isolated from porcine spinal and determined the structure by H. Matsuo et al. as shown in Biochem. Biophys. Res. Commun., 1985, 130, 1078.

As shown in FIG. 2, the protected form of Neuromedin U-25 was prepared by successive azide condensation of six sections of peptides. Then, the protected form of Neuromedin U-25 was treated with the deprotecting reagent composed of 1M trimethylsilyltrifluoromethanesulfonate and thioanisole/trifluoroacetic acid system with presence of methacresol and ethanediol at 0° C. for 60 minutes to remove all of the protective groups. The liquid was adjusted to pH 8.0 with 5% aqueous ammonia and treated with ammonium fluoride at 0° C. for 30 minutes to hydrolyze trimethylsilylated compounds and reverse any possible N→O shift at the residues of Ser. The product thus treated was then subjected to gel-filtration on SephadexG-25(trade name: manufactured and sold by Pharmacia), and then purified through high performance liquid chromatography (using TSK-GEL LS-410 KG column) to obtain highly purified Neuromedin U-25 in a high yield of 52%.

On the other hand, the same procedures as those described above were repeated except that trifluoromethanesulfonic acid was used instead of trimethylsilyltrifluoromethanesulfonate and that the treatment was continued for 150 minutes. This resulted in an yield of only 47%

DEPROTECTION IN SYNTHESIS OF RABBIT STOMACH PEPTIDE

The Rabbit Stomach Peptide is octapeptide having the amino acid sequence shown in FIG. 3 (b). The protected peptide resin was prepare according to a method of Merrifield shown in J. Amer. Chem. Soc., 1963, 85, 2149 by P. B. Merrifield. The structure of this protected peptide resin is shown in FIG. 3(a).

The protected peptide resin was first suspended in thioanisole/trfluoroacetic acid, 1M trimethylsilyltrifluoromethanesulfonate was added thereto in an ice bath and stirred for 60 minutes followed by filtration to remove the resin. The resin was adjusted to pH 8 with 5% ammonia in an ice bath, then was treated with ammonium fluoride for 10 minutes and subjected to gel-filtration on Sephadex G-10, followed by purification through high performance liquid chromatography (on the same column as used before). This deprotection reaction scheme is shown in FIG. 3. As a result, the Rabbit Stomach Peptide was recovered in an yield of 27%. The chart of this high performance liquid chromatography is shown in FIG. 4.

The same deprotection reaction was repeated using 1M trifluoromethanesulfonic acid and thioanisole/trifluoroacetic acid system in place of trimethylsilyltrifluoromethanesulfonate and the reaction was continued for 120 minutes at 0° C. As a result of recovering, the yield thereof was low only 16%.

DEPROTECTION IN SYNTHESIS OF GALANIN

Galanin contains Asp-Asn sequences, which tend to cause an amino-succinimide type side reaction, also contains Trp residue as shown in FIG. 5(b). The indole nucleas of Trp residue is liable to be attacked with alkaline cations and, therefore, the synthesis of Trp-containing peptides is relatively difficult. However, Galanin could be obtained in a sufficient yield by the use of a deprotecting reagent of 1M trimethylsilyltrifluoromethanesulfonate and thioanisole/trifluoroacetic acid system in the synthesis of Galanin.

First of all, the protected Galanin shown in FIG. 5(a) was treated with 1M trimethylsilyltrifluoromethanesulfonate and thioanisole/trifluoroacetic acid system with presence of metacresol and ethanediol at 0° C. for 120 minutes to remove all of the protective groups. Thereafter, the product was treated as before and crude Galanin was obtained in 86% yield after gel-filtration. The crude Galanin was subjected to high performance liquid chromatography, a chart of which was shown in FIG. 6. As seen from the chromatogram, the purity of Galanin is 81%. Thus, it is found that the reagent of the present invention can be used to prepare peptides containing Asp, Trp residues without any problem.

DEPROTECTION IN SYNTHESIS OF UROTENSIN II

The reagent according to the present invention was used in synthesis of Urotensin II shown in FIG. 7(c) as a model of Cys containing peptide.

The protected form of Urotensin II was first treated with $Tl(CF_3COOH)_3$ as shown in FIG. 7(a) to (b) to remove protective groups of Cys and thus form disulfides. Then, the remaining protective groups were removed with 1M trimethylsilyltrifluoromethanesulfonate and diphenylsulfide/trifluoroacetic acid system shown in FIG. 7(b) to (c) and the product was subjected to gel-filtration on Sephadex G-10 to obtain crude Urotensin II. The crude Urotensin II was then subjected to high performance liquid chromatography, a chart of which was shown in FIG. 8. The isolation yield attained after high performance liquid chromatography was 15% which is approximately identical to that achieved in the synthesis of Cys-containing peptide using the conventional deprotecting reagent, i.e., trifluoromethanesulfonic acid. Thus, it was evidenced that the reagent of the present invention could effectively be applied to the synthesis of Cys containing peptides.

Although the embodiments of this invention has been disclosed and described, it is apprent that other embodiments of the invention are possible.

What is claimed is:

1. A reagent for removing protective groups attached to an amino acid during peptide synthesis which comprises trifluoroacetic acid and a combination of hard acid and soft base, where the hard acid is trialkylsilyltrifluoromethanesulfonate having the formula $R_3SiO_3SCF_3$ in which the R is an alkyl group and the soft base is an ether selected from the group consisting of anisole, thioanisole, and diphenylsulfide.

2. The reagent of claim 1, where the hard acid is trimethylsilyltrifluoromethanesulfonate.

3. The reagent of claim 1, where the ether is thioanisole.

4. The reagent of claim 1, further comprising metacresol.

5. The reagent of claim 1, further comprising ethanediol.

6. The reagent of claim 1, where the hard acid is trimethylsilyltrifluoromethanesulfonate, the ether is thioanisole, and the regent further comprises metacresol and ethanediol.

* * * * *